United States Patent [19]

Adamson et al.

[11] Patent Number: 5,013,718

[45] Date of Patent: May 7, 1991

[54] METHOD FOR TREATING IRON OVERLOAD USING EPO

[75] Inventors: John W. Adamson, Bainbridge Island; Joseph W. Eschbach, Bellevue, both of Wash.; Michael R. Downing; Joan C. Egrie, both of Thousand Oaks, Calif.

[73] Assignee: Amgen, Inc., Thousand Oaks, Calif.

[21] Appl. No.: 933,495

[22] Filed: Nov. 21, 1986

[51] Int. Cl.$^5$ .................. C07K 37/24; C07K 37/36
[52] U.S. Cl. ........................................... 514/8; 514/2; 514/21; 604/6; 604/52; 604/53
[58] Field of Search ................. 530/399; 514/2, 8, 21; 604/6, 52, 53

[56] References Cited

U.S. PATENT DOCUMENTS 4,667,016  5/1987  Lai et al. ............................. 530/397
4,703,008  10/1987  Lin ..................................... 435/240.2

OTHER PUBLICATIONS

J. Clin. Invest., 74 (1984), 434–441, Eschbach et al.

Primary Examiner—Howard E. Schain
Attorney, Agent, or Firm—Steven M. Odre; Daniel M. Chambers

[57] ABSTRACT

A method for reducing stored iron and serum iron in mammals is disclosed. In particular, a mammal having an iron overload disorder is administered a therapeutically effective amount of erythropoietin to increase red blood cell production and the mammal is subsequently phlebotomized to remove the excess red blood cells produced.

8 Claims, No Drawings

METHOD FOR TREATING IRON OVERLOAD USING EPO

BACKGROUND

The present disclosure relates to a method for reducing iron overload in mammals having elevated stored iron and serum iron levels. In particular, the disclosure relates to a method for treating mammals having an iron overload disorder and functioning bone marrow capable of producing red blood cells upon treatment with erythropoietin.

Hemochromatosis is a generic term associated with iron overload disorders wherein excessive iron absorption and/or parental iron loading results in parenchymal deposition of iron with eventual tissue damage. Commonly associated with hemochromatosis are an increase in total body iron stores, deposition of large quantities of iron in the form of ferritin and hemosiderin in the parenchymal cells of the heart, pancreas, liver and other organs, and morphologic and functional damage to the organs and sites being exposed to excess iron deposition. Factors leading to iron overload may include, for example, hereditary hemochromatosis, dietary hemochromatosis, erythropoietic hemochromatosis, and transfusion-induced hemochromatosis. Most manifestations of hemochromatosis, i.e., arthritis, diabetes, arrhythmias, congestive failure and the like are treated by conventional means. Specific therapy for a patient suffering from hemochromatosis is removal of excess iron. The most common procedure for removing excess iron from the body is phlebotomy. The aim of phlebotomy is to remove iron in amounts sufficient to reverse iron overload in parenchymal cells Wintrobe, et al. *Clinical Hematology*, 8th Edition, p 667-676. Typical phlebotomy treatments provide for the removal of approximately one pint of blood weekly or twice weekly. In a typical patient it will require approximately one year to remove accumulated iron overload which averages approximately 25 g [Crosby, Hemochromatosis: the unsolved problems, Sem Hematol 14:135,1977].

Erythropoietin is a glycoprotein hormone having an apparent molecular weight of about 36,000 daltons. It is produced and secreted primarily in the kidney and acts on precursor cells of erythrocytes to differentiate them into erythrocytes. It is useful as a therapeutic agent for anemia caused by renal insufficiency, for preparation of clinical diagnostic reagents, and as a reagent for research in hematopoiesis. Erythropoietin may be purified from human urine *J. Biol. Chem.*, 252(15) 5558-5564 (1977)]. Recombinant erythropoietin may be produced by genetic engineering methods (see, e.g., U.S. Pat. No. 4,703,008) and may be purified in accordance with procedures described in pending U.S. application Ser. No. 747,119 filed June 20, 1985. now U.S. Pat. No. 4,667,016.

SUMMARY

The present invention relates to a method for reducing stored iron and serum iron in a mammal having an iron overload disorder comprising administering to the mammal a therapeutically effective amount of erythropoietin and phlebotomizing the mammal to remove excess red blood cells. The method of the present invention is effective in reducing stored iron and serum iron in mammals having an iron overload disorder and functioning bone marrow capable of producing red blood cells upon treatment with a therapeutically effective amount of erythropoietin. It has been found that the method of the present invention is effective in reducing elevated iron stores and serum iron levels to normal levels in a treated mammal.

DETAILED DESCRIPTION

In accordance with the method of the present invention, a patient suffering from an iron overload disorder and capable of producing red blood cells, is administered a therapeutically effective amount of erythropoietin. As previously mentioned, a patient treated in accordance with the method of the present invention must have a functioning bone marrow capable of producing red blood cells. The erythropoietin stimulates the production of red blood cells and thus the demand for red blood cell synthesis imposed by the administration of therapeutically effective amounts of erythropoietin significantly decreases the levels of stored iron in the body. Subsequent phlebotomy of a patient treated with erythropoietin provides removal of the excess red blood cells produced and thereby effectively reduces levels of stored iron and serum iron.

As used herein, the term "therapeutically effective amount of erythropoietin" refers to the amount of naturally derived or recombinantly produced erythropoietin sufficient to increase the production of red blood cells. Such amounts are readily ascertained by one of ordinary skill in the art and may depend upon the particular individual being treated, the specific condition being treated, severity of the condition, administration regimen to be followed and the like. It has been found that administration of recombinantly produced erythropoietin in a range of from 15-1,500 units/kg. body weight and preferably from 50-300 units/kg. body weight has been effective in increasing red blood cell production and in reducing iron overload in patients suffering from renal failure disease. In addition, it has been found that doses of recombinant erythropoietin equal to or greater than 15 units/body weight are required to increase productioon of red blood cells in patients suffering from renal failure disease. Although naturally derived erythropoietin may be employed, it is preferred to employ recombinantly produced erythropoietin. The erythropoietin may be formulated as desired in accordance with techniques readily ascertained by one of ordinary skill in the art. It is preferred to formulate recombinant erythropoietin in a buffered saline solution.

Upon administration of a therapeutically effective amount of erythropoietin, the red blood cell production of the treated patient will increase. When the hematocrit level has increased to a level above the normal range for the particular patient, phlebotomy is conducted. In accordance with the method of the present invention, the frequency of phlebotomy and amount of red blood cells removed during each phlebotomy treatment is readily ascertained by one of ordinary skill in the art and will depend on, for example, the particular patient, the hematocrit of the patient, normal hematocrit level of the particular patient, dose of erythropoietin, frequency of erythropoitin treatment, severity of the condition and the like. Alternatively another embodiment of the present invention provides that if a patient has iron overload and a normal or near normal hematocrit, it may be preferred to phlebotomize the patient initially to lower the hematocrit to a level below normal and then administer a therapeutically effective amount of erythropoietin to increase the rate of red blood cell production in order to restore the hematocrit to normal levels.

The term "iron overload disorders" refers to a condition wherein the stored iron and serum iron exceed the normal levels. Generally, total body iron stores are maintained normally within a range of 0.2–1.5 g. [Clin. Physiol. Biochem. 4:61–77 (1986)]. Iron overload disorders treatable by the method of the present invention include conditions wherein the patient has functioning bone marrow and thus is capable of producing red blood cells, such as for example transfusion-induced hemotochromatsis associated with chronic anemia resulting from renal function failure.

The method of the present invention enables a patient suffering from an iron overload disorder to substantially increase his or her rate of red blood cell production thereby increasing frequency rate at which phlebotomy may be conducted and/or the amount of red blood cells removed during phlebotomy. Increasing the frequency at which a patient may be phlebotomized and/or the amount of red blood cells removed during phlebotomy in accordance with the present invention will significantly decrease the time required to reduce excess stored iron and serum iron when compared to conventional procedures which use only phebotomy. Thus the method of the present invention is particularly effective in treating iron overload disorders wherein high excess levels of stored iron are present and it is necessary to quickly reduce the stored iron to normal levels.

The techniques available for determining excessive parenchymal iron stores include (1) measurement of serum iron, (2) determination of percent saturation of transferrin, (3) estimation of chelatable iron stores using the agent desferrioxamine, (4) measurement of serum ferritin concentration and (5) liver biopsy. The serum iron level and percent saturation of transferrin are elevated early in the course of the disease, but their specificity is reduced by relatively high false-positive and false-negative rates. In untreated patients having hemochromatosis, the serum ferritin level is greatly increased. Therefore, measurement of serum ferritin is generally useful as a noninvasive screening test for the diagnosis of early disease, since it is usually abnormal before there is any morphological evidence of liver damage and the ferritin concentration correlates with the magnitude of body iron stores. In clinical practice, the combined measurements of the (1) serum iron concentration, (2) percent transferrin saturation, and (3) serum ferritan level provide the simplest and most reliable screening test for hemochromatosis [Isselbacher et al, Harrison's Principle of Internal Medicine, 9th Edition, p. 490].

The following example will further illustrate the invention although it will be understood that the invention is not limited to this specific example.

EXAMPLE 1

Twenty-three anemic, hemodialysis patients have been treated with recombinant human erythropoietin. The recombinant human erythropoietin was administered as an intravenous bolus three times weekly beginning within 12 hours of the end of dialysis in doses of 15, 50, 150, 500 or 1,500 units/kg. Transfusion requirements, reticulocyte responses, hematocrit and ferrokinetics were monitored. Serum samples were drawn and the serum ferritin, serum iron and transferrin saturation levels were measured. The serum ferritin levels were determined in accordance with the procedure described in Lipschitz, D.A. et al, "A Clinical Evaluation of Serum Ferritin as an Index of Iron Stores," New England Journal of Medicine, Vol. 290, p 1213–1216 (1974). The results obtained are represented in Table I:

TABLE I

Changes in Iron Balance With Recombinant Erythropoietin Therapy

| Patient No. | Dose (Units/kg) | Duration of Therapy (wks) | Serum Iron ($\mu$g/dl) Before Therapy | Serum Iron ($\mu$g/dl) Following Therapy | Transferrin Saturation (%) Before Therapy | Transferrin Saturation (%) Following Therapy | Ferritin (ng/ml) Before Therapy | Ferritin (ng/ml) Following Therapy |
|---|---|---|---|---|---|---|---|---|
| 1 | 15 | 17 | 219 | 174 | 92 | 87 | 3,586 | 2,184 |
| 2 | 15 | 14 | 100 | 60 | 36 | 21 | 818 | 478 |
| 3 | 15 | 9 | 39 | 37 | 15 | 13 | 1,059 | 675 |
| 4 | 50 | 12 | 147 | 38 | 52 | 13 | 885 | 578 |
| 5 | 50 | 11 | 65 | 33 | 27 | 12 | 139 | 18 |
| 6 | 50 | 9 | 79 | 41 | 22 | 13 | 111 | 30 |
| 7 | 50 | 6 | 214 | 44 | 88 | 20 | 2,301 | 1,457 |
| 8 | 150 | 6 | 63 | 38 | 25 | 12 | 459 | 101 |
| 9 | 150 | 13 | 229 | 178 | 100 | 92 | 5,738 | 3,797 |
| 10 | 150 | 10 | 228 | 78 | 77 | 28 | 900 | 219 |
| 11 | 150 | 12 | 145 | 86 | 75 | 47 | 2,875 | 2,341 |
| 12 | 150 | 4 | 107 | 43 | 52 | 20 | 1,482 | 1,073 |
| 13 | 500 | 3 | 102 | 44 | 40 | 18 | 738 | 344 |
| 14 | 500 | 6 | 60 | 30 | 19 | 9 | 333 | 28 |
| 15 | 500 | 5 | 149 | 28 | 59 | 15 | 2,009 | 1,094 |
| 16 | 500 | 4 | 86 | 61 | 33 | 32 | 672 | 313 |
| 17 | 500 | 5 | 109 | 37 | 39 | 17 | 1,266 | 400 |
| 18 | 1,500 | 4 | 68 | 90 | 25 | 38 | 536 | 148 |
| 19 | 1,500 | 5 | 136 | 107 | 52 | 35 | 53 | 13 |
| 20 | 1,500 | 4 | 59 | 33 | 24 | 17 | 556 | 95 |
| 21 | 1,500 | 5 | 54 | 77 | 19 | 31 | 426 | 77 |
| 22 | 1,500 | 3 | 111 | 76 | 43 | 39 | 1,545 | 95 |

Various other examples and modifications of the foregoing description and examples will be apparent to a person skilled in the art after reading the present disclosure without departing from the spirit and scope of the invention, and it is intended that all such examples or modifications be included within the scope of the appended claims.

WHAT IS CLAIMED IS:

1. A method for reducing stored iron and serum iron in a mammal having an iron overload disorder comprising:
   (a) administering to the mammal a therapeutically effective amount of human erythropoietin; and
   (b) phlebotomizing the mammal.

2. A method according to claim 1 wherein the erythropoietin is recombinantly produced human erythropoietin.

3. A method according to claim 2 wherein the therapeutically effective amount of recombinantly produced human erythropoietin is equal to or greater than 15 units/kg. body weight.

4. A method according to claim 3 wherein the therapeutically effective amount of recombinantly produced human erythropoietin is from about 50 to 300 units/kg. body weight.

5. A method for reducing stored iron and serum iron in a mammal having an iron overload disorder comprising: (a) phlebotomizing the mammal; and (b) administering to the mammal a therapeutically effective amount of human erythropoietin.

6. A method according to claim 5 wherein the erythropoietin is recombinantly produced human erythropoietin.

7. A method according to claim 6 wherein the therapeutically effective amount of recombinantly produced human erythropoietin is equal to or greater than 15 units/kg. body weight.

8. A method according to claim 7 wherein the therapeutically effective amount of recombinantly produced human erythropoietin is from about 50 to 300 units/kg. body weight.

* * * * *